(12) United States Patent
Miao et al.

(10) Patent No.: US 10,071,180 B1
(45) Date of Patent: Sep. 11, 2018

(54) DEVICES AND SYSTEMS FOR AN ILLUMINATED SURGICAL SUTURE

(71) Applicant: Verily Life Sciences LLC, Mountain View, CA (US)

(72) Inventors: Xiaoyu Miao, Palo Alto, CA (US); Douglas Weibel, Madison, WI (US); Babak Parviz, Los Altos, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 769 days.

(21) Appl. No.: 14/289,352

(22) Filed: May 28, 2014

(51) Int. Cl.
| | |
|---|---|
| *A61B 17/04* | (2006.01) |
| *A61L 17/00* | (2006.01) |
| *A61B 17/06* | (2006.01) |
| *A61B 90/30* | (2016.01) |
| *A61B 90/00* | (2016.01) |

(52) U.S. Cl.
CPC .......... *A61L 17/00* (2013.01); *A61B 17/0482* (2013.01); *A61B 17/06066* (2013.01); *A61B 90/30* (2016.02); *A61B 90/361* (2016.02)

(58) Field of Classification Search
CPC ....... A61L 17/00; A61B 90/361; A61B 90/30; A61B 17/0482; A61B 17/06066
See application file for complete search history.

(56) References Cited

U.S. PATENT DOCUMENTS

| | | | | |
|---|---|---|---|---|
| 5,432,876 A | * | 7/1995 | Appeldorn | G02B 6/001 362/554 |
| 2001/0040973 A1 | * | 11/2001 | Fritz | A61B 5/6817 381/322 |
| 2008/0132942 A1 | * | 6/2008 | Mueller | A61B 17/0401 606/228 |
| 2011/0125188 A1 | * | 5/2011 | Goraltchouk | A61B 17/06166 606/228 |

(Continued)

FOREIGN PATENT DOCUMENTS

| | | |
|---|---|---|
| EP | 482960 A1 | 4/1992 |
| EP | 2700365 A1 | 2/2014 |

OTHER PUBLICATIONS

USP Monographs: Absorbable Surgical Suture, http://www.pharmacopeia.cn/v29240/usp29nf24s0_m80190.html, Jan. 1, 2007.

(Continued)

*Primary Examiner* — Richard Louis
(74) *Attorney, Agent, or Firm* — McDonnell Boehnen Hulbert & Berghoff LLP

(57) ABSTRACT

An apparatus may comprise an optical fiber that includes a core region having a core thickness and a cladding layer having a cladding layer thickness. The core region and the cladding layer may have material characteristics suitable for suturing biological tissue. The core thickness and the cladding layer thickness may be configured to cause at least a portion of light propagating in the core region to propagate out of the optical fiber through the cladding layer. The (Continued)

apparatus may also comprise a light source optically coupled to the optical fiber and configured to provide the light for propagation in the core region of the optical fiber. The apparatus may also comprise a suturing device coupled to the optical fiber and configured to guide the optical fiber for suturing the biological tissue.

18 Claims, 8 Drawing Sheets

(56) References Cited

U.S. PATENT DOCUMENTS

| | | | |
|---|---|---|---|
| 2011/0319932 A1* | 12/2011 | Avelar | A61B 17/0469 606/228 |
| 2012/0136388 A1* | 5/2012 | Odermatt | A61B 17/06166 606/222 |
| 2012/0165759 A1 | 6/2012 | Rogers et al. | |
| 2012/0244143 A1 | 9/2012 | Lo et al. | |

OTHER PUBLICATIONS

How suture is made, http://www.madehow.com/Volume-7/Suture.html, Aug. 9, 2012.

* cited by examiner

US 10,071,180 B1

DEVICES AND SYSTEMS FOR AN ILLUMINATED SURGICAL SUTURE

BACKGROUND

Unless otherwise indicated herein, the materials described in this section are not prior art to the claims in this application and are not admitted to be prior art by inclusion in this section.

A surgical suture is a medical device that may be utilized to hold or stitch biological tissue after an injury or a surgery. For example, during manual or robotic laparoscopic surgery, a surgeon may utilize the suture for stitching damaged biological tissue to allow the biological tissue to heal. In some examples, the suture may include absorbable materials that decompose over time as the biological tissue heals. In other examples, the suture may include non-absorbable materials. In these examples, the suture may be removed after the biological tissue heals. In some examples, the suture may include natural or synthetic materials that have material characteristics suitable for suturing the biological tissue.

SUMMARY

In one example, an apparatus is provided that includes an optical fiber. The optical fiber may include a core region having a core thickness and a cladding layer having a cladding layer thickness. The core region and the cladding layer may have material characteristics suitable for suturing biological tissue. The core thickness and the cladding layer thickness may be configured to cause at least a portion of light propagating in the core region to propagate out of the optical fiber through the cladding layer. The apparatus also includes a light source optically coupled to the optical fiber and configured to provide the light for propagation in the core region of the optical fiber. The apparatus also includes a suturing device coupled to the optical fiber and configured to guide the optical fiber for suturing the biological tissue.

In another example, a suture is provided that includes a core polymer having a core thickness. The core polymer may have a core index of refraction to allow light to propagate in the core polymer. The suture also includes a cladding polymer having a cladding thickness. The cladding polymer may be coupled to an outer surface of the core polymer. The cladding polymer may have a cladding index of refraction such that a first portion of the light propagating in the core polymer is guided inside the core polymer. The core thickness and the cladding thickness may be configured to cause a second portion of the light propagating in the core polymer to propagate through the cladding polymer to illuminate the suture. The core polymer and the cladding polymer may have material characteristics suitable for suturing biological tissue.

In yet another example, a suturing device is provided. The suturing device includes a surgical needle having an indentation to couple an optical fiber. The optical fiber may include a core region having a core thickness and a cladding layer having a cladding layer thickness. The core region and the cladding layer may have material characteristics suitable for suturing biological tissue. The core thickness and the cladding layer thickness may be configured to cause at least a portion of light propagating in the core region to propagate out of the optical fiber through the cladding layer. The suturing device also includes a light source disposed on the surgical needle. The light source may be optically coupled to the optical fiber and configured to provide the light for propagation in the core region of the optical fiber.

These as well as other aspects, advantages, and alternatives, will become apparent to those of ordinary skill in the art by reading the following detailed description, with reference where appropriate to the accompanying figures.

DETAILED DESCRIPTION

Figure 1:
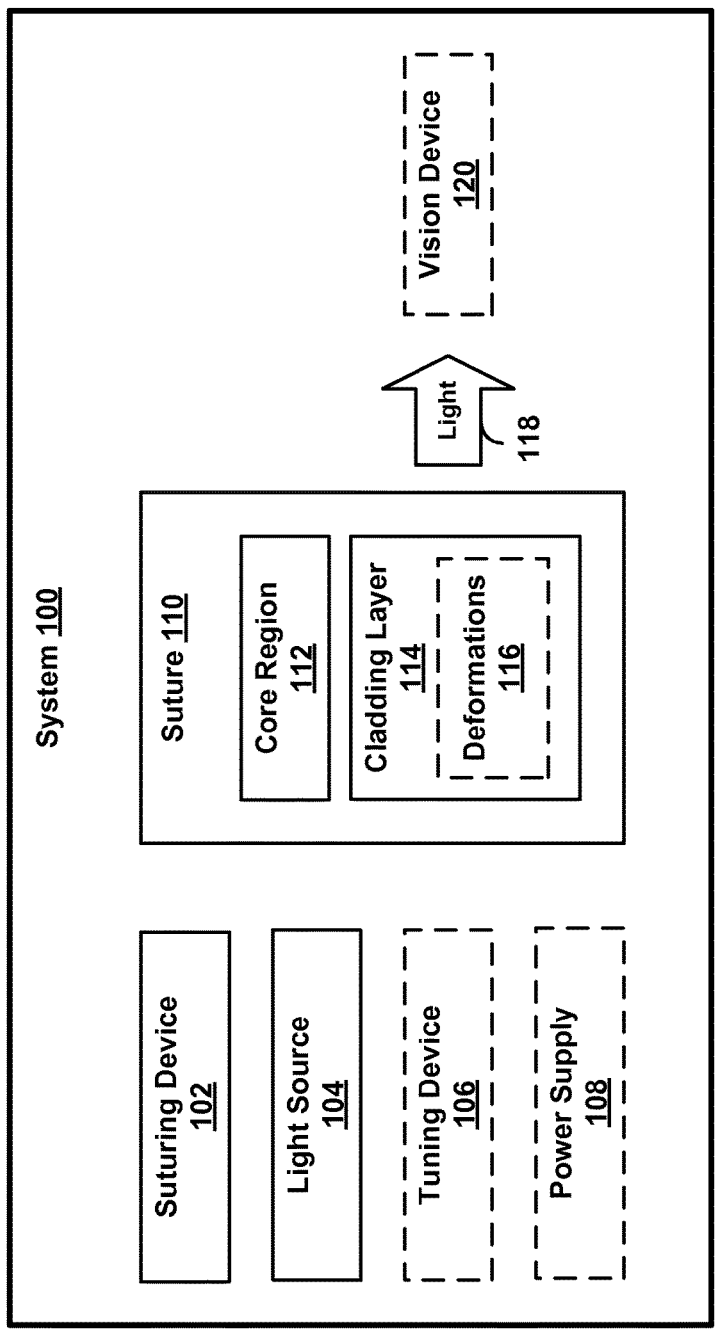
FIG. 1 is a block diagram of a system for suturing biological tissue, according to an example embodiment.

The following detailed description describes various features and functions of the disclosed systems and methods with reference to the accompanying figures. In the figures, similar symbols identify similar components, unless context dictates otherwise. The illustrative system, device and method embodiments described herein are not meant to be limiting. It may be readily understood by those skilled in the art that certain aspects of the disclosed systems, devices and methods can be arranged and combined in a wide variety of different configurations, all of which are contemplated herein.

In some scenarios, accurate placement of a surgical suture on biological tissue may be challenging due to the suture being placed in a region that is difficult to observe. In one example, a color of the biological tissue may be similar to a color of the suture. In another example, the region where the suture is placed may be dark. Further, in some examples, utilizing an optic probe that includes a light source to observe the placement of the suture may be difficult. For example, the region where the suture is placed may not include a sufficiently large open space to receive the optic probe as well as a suturing device for the placement of the suture.

Within examples, devices and systems are provided that include an illuminated surgical suture for suturing biological tissue. Such suture, for example, may have material characteristics suitable for suturing the biological tissue. Example material characteristics may include strength, flexibility, diameter, absorbability, lack of toxicity, etc.

In one example, an apparatus is provided that includes an optical fiber configured as a suture. For example, the optical fiber may have material characteristics suitable for suturing biological tissue. The optical fiber may include a core region that has a core index of refraction and a cladding layer coupled to an outer surface of the core region that has a cladding index of refraction. In turn, for example, a first portion of light propagating in the core region may be guided inside the core region. Further, for example, a core thickness of the core region and a cladding layer thickness of the cladding layer may be configured to allow a second portion of the light to propagate through the cladding layer to illuminate the optical fiber. The apparatus also includes a light source optically coupled to the optical fiber and configured to provide the light for propagation in the core region. The apparatus also includes a suturing device, such as a surgical needle, coupled to the optical fiber and configured to guide the optical fiber for suturing the biological tissue.

Additionally, some embodiments of the present disclosure provide systems and methods to further enhance visibility of the suture. In one example, a tuning device may be coupled to the light source to allow modulating the light provided by the light source. In this example, various aspects of the light such as intensity, color, frequency, pattern, etc. may be modulated to enhance the visibility or to increase contrast between the suture and the biological tissue being sutured. In another example, the cladding layer may include a plurality of deformations to facilitate propagation of the second portion of the light out of the cladding layer. Other examples are possible and are described in exemplary embodiments of the present disclosure.

Referring now to the Figures, FIG. 1 is a block diagram of a system 100 for suturing biological tissue, according to an example embodiment. The system 100 includes a suturing device 102, a light source 104, and a suture 110. In some examples, the system 100 may optionally include a tuning device 106, a power supply 108, and/or a vision device 120.

The suturing device 102 may be configured to guide the suture 110 for suturing the biological tissue. In some examples, the suturing device 102 may include a surgical needle formed from a solid material such as steel, plastic, composite, metal, or any other material configured to couple with the suture 110 and guide the suture 110 for placement on the biological tissue. For example, the suturing device 102 may include a sharp edge having a particular diameter to stitch the biological tissue without causing significant damage (e.g., indenting, blanching, etc.) to the biological tissue. Additionally, in some examples, the surgical needle (suturing device 102) may be configured in various geometric shapes such as straight, ¼ circle, ⅜ circle, ½ circle, ⅝ circle, compound curve, half curved, half curved at both ends of a straight segment, etc. Other geometric shapes associated with a point geometry of the suturing device 102 are also possible such as taper (needle body is round and tapers smoothly to a point), cutting (needle body is triangular and has a sharpened cutting edge on the inside curve), reverse cutting (cutting edge on the outside), tapercut (needle body is round and tapered, but ends in a small triangular cutting point), blunt points (e.g., for suturing friable tissues), side cutting (flat on top and bottom with a cutting edge along the front to one side), etc.

In some examples, the surgical needle (suturing device 102) may include an indentation for coupling the suture 110 to the suturing device 102. For example, the indentation may correspond to a hole drilled in the surgical needle having dimensions to allow insertion of the suture 110. For example, the indentation may be crimped onto the suture 110 to couple the suture 110 with the suturing device 102 (e.g., swaging, etc.).

Additionally, in some examples, various techniques may be employed by the suturing device 102 to guide the suture 110 such as interrupted stitch (e.g., vertical mattress stitch, horizontal mattress stitch, etc.) or continuous stitch in accordance with a desired tension distribution of the suturing.

Although not illustrated in FIG. 1, in some examples, the suturing device 102 may include or may be coupled to additional components for use in a robotic surgery. For example, the suturing device 102 may include a computing device coupled to a robotic arm. The computing device may execute program instructions in data storage of the computing device to cause the robotic arm to guide the suture 110 for suturing the biological tissue. Additionally, in some examples, the suturing device 102 may include an apparatus for tying part of the suture 110 into a knot (e.g., square knot, surgeon knot, etc.) after the biological tissue is sutured. Such apparatus, in some examples, may also be operated by the computing device.

The light source 104 may be optically coupled to the suture 110 and configured to provide light for propagation inside the suture 110. In one example, the light source 104 may be disposed on the suturing device 102 proximal to the suture 110. For example, the light source 104 may be disposed inside or adjacent to an indentation of a surgical needle (e.g., the suturing device 102) where the suture 110 is coupled to the surgical needle. In another example, the light source 104 may be disposed on the suture 110. For example, the light source 104 may be positioned at one or both ends of the suture 110. The light source 104 may include one or more light emitting diodes (LED), vertical cavity surface emitting lasers (VCSEL), organic light emitting diodes (OLED), polymer light-emitting diodes (PLED), light emitting polymers (LEP), liquid crystal displays (LCD), microelectromechanical systems (MEMS), fluorescent dye, resistive filament, or any other light source configured to transmit the light for propagation inside the suture 110. In some examples, the light source 104 may be configured to provide visible light. In other examples, the light source 104 may be configured to provide non-visible light (e.g., infrared, ultraviolet, x-ray, etc.).

Additionally or alternatively, in some examples, the light source 104 and the suture 110 (or the suturing device 102) may be implemented as the same physical component. For example, organic materials (e.g., organometallic chelates, fluorescent dyes, phosphorescent dyes, conjugated dendrimers, other light emitting organic materials, etc.) can be patterned on the suturing device 102 and/or the suture 110 to form the light source 104 (e.g., OLED, PLED, etc.).

Further, in some examples, the light source 104 may be configured to process ambient light to provide the light for propagation in the suture 110. For example, the light source 104 may include a substantially transparent liquid crystal material positioned at one or both ends of the suture 110, and arranged to direct ambient light into the suture 110. Thus, in this example, the light provided by the light source 104 may be due to chemical properties of the liquid crystal material. Additionally or alternatively, in some examples, the light source 104 may include an array of LEDs configured to provide the light including multiple colors, intensities, wavelengths, other modulations, etc.

Although not illustrated in FIG. 1, in some examples, the light source 104 may also include one or more optical elements to direct and/or adjust the light into the suture 110. Alternatively, in some examples, the one or more optical elements may be implemented as separate physical components arranged to receive the light from the light source 104 and to direct the light into the suture 110. In some examples, the one or more optical elements may include lens, mirrors, prisms, filters, or any other optical element.

The tuning device 106 may be optionally included in the system 100 and coupled to the light source 104 to modulate light provided by the light source 104. In some examples, the modulation may correspond to the tuning device 106 controlling the light source 104. For example, the tuning device 106 may be configured to adjust one or more of a wavelength or intensity of the light provided by the light source 104. Additionally or alternatively, in some examples, the modulation may correspond to the tuning device 106 controlling an optical element (e.g., filter, polarizer, shutter, diffraction grating, etc.) through which light from the light source 104 is transmitted to the suture 110. In some examples, the tuning device 106 may receive an input indicative of a modulation of the light provided by the light source 104. For example, the tuning device 106 may include or may be coupled to one or more input devices such as knobs, buttons, other user interface device, etc., that is configured to provide the input. For example, a human operator (e.g., surgeon, technician, etc.) or a computer operator (e.g., robotic surgery platform, etc.) of the system 100 may provide the input indicative of the modulation. For example, the biological tissue being sutured may have a given color (e.g., red, etc.), and the input may cause the tuning device 106 to modulate the light provided by the light source 104 to a different color (e.g., yellow, etc.) to provide a contrast with the given color and enhance visibility of the suture 110. Further, for example, the operator of the system 100 (e.g., surgeon) may utilize the tuning device 106 (e.g., via knob) to adjust the color and/or intensity of the modulated light provided by the light source 104 according to a preference of the operator.

In some examples, the tuning device 106 may be configured to provide light from the light source 104 in a given modulated light pattern. For example, the tuning device 106 may be configured to intermittently change the modulation of the light (e.g., color, intensity, etc.) provided by the light source 104 to provide a dynamic trace of the suture 110 (e.g., a visualization of a path of the suture 110) during placement of the suture. Such dynamic trace, for example, may improve visibility of the suture 110. Further, in some examples, the given modulated light pattern may be indicated by program instructions configured to be executed by a processor to cause the tuning device 106 to modulate the provided light by the light source 104 in accordance with the given modulated light pattern. In one example, the tuning device 106 may include a plurality of buttons that correspond to a plurality of light modulation schemes, and selecting a given button may provide the input indicative of the given modulated light pattern. Other examples are possible as well.

The power supply 108 may be optionally included in the system 100 to power the suturing device 102, the light source 104, and/or other components of the system 100. In some examples, the power supply 108 may include one or more energy storage devices such as electrochemical cells, capacitors, super capacitors, etc., electrically coupled to the light source 104 and/or the other components of the system 100 to provide the power. Additionally or alternatively, in some examples, the power supply 108 may include energy-harvesting components such as energy-harvesting antennas to capture incident radio radiation, or photovoltaic cells (e.g., solar cells) to capture energy from incoming light (e.g., visible, ultraviolet, infrared, and/or other light). For example, the incoming light may include ambient light in the environment of the system 100 or may be transmitted by an external light source (not illustrated in FIG. 1) towards the photovoltaic cells (e.g., the power supply 108). Further, in some examples, the power supply 108 may include a wired connection (e.g., USB, power cable, etc.) to an external power source (e.g., computing device, power outlet, etc.). Additionally, in some examples, the power supply 108 may include various components such as rectifiers and/or transformers to provide a regulated power signal (e.g., DC voltage, etc.) to the light source 104 and/or other components of the system 100.

In some examples, the power supply 108 may be configured to provide the power to the light source 104 and/or other components of the system 100 in response to detection of oxygen. In an example scenario, parts or all of the system 100 such as the suturing device 102, the light source 104, the suture 110, the power supply 108, etc., may be sterilized and packaged in a vacuum-sealed container prior to the suturing of the biological tissue. In the example scenario, the power supply 108 may include a sensor configured to detect oxygen when the container is opened and, in turn, activate the power supply 108 to power one or more components (e.g., the light source 104) of the system 100.

The suture 110 may be configured as an optical fiber having material characteristics suitable for the suturing of the biological tissue. In turn, the suture 110 includes a core region 112 and a cladding layer 114. The core region 112 and the cladding layer 114 may be formed from materials having the suitable material characteristics. Example material characteristics may include strength, flexibility, diameter, absorbability, lack of toxicity, antimicrobial characteristics, elasticity, etc. Suitable materials, for example, may be defined in a medical pharmacopeia that includes a listing of the materials and/or a specification of the suitable material characteristics of such medical devices (e.g., the suture 110). However, in some examples, the suture 110 may include given materials other than the materials indicated by the medical pharmacopeia, such as the given materials that have some or all of the suitable material characteristics.

In some examples, the core region 112 and the cladding layer 114 may include absorbable or non-absorbable materials. The absorbable materials, for example, may include materials that gradually degrade (e.g., decompose, dissolve, react with biological fluids/enzymes, etc.) as the biological tissue heals after the suturing. A non-exhaustive list of possible absorbable materials may include polyglycolic acid, polylactic acid, polydioxanone, polycaprolactone, glycolide-lactide copolymer, or any other polymer/copolymer that has the absorbable material characteristics. On the other hand, for example, the non-absorbable materials may include materials that do not degrade or that may degrade over a longer period of time. Thus, in an example scenario where the suture 110 includes the non-absorbable materials, the suture 110 may be removed from the biological tissue after the biological tissue heals. A non-exhaustive list of possible non-absorbable materials may include polypropylene, polyester, nylon, polyethylene terephthalate, polybutylene terephthalate, polyamide, or any other polymer/copolymer that has the non-absorbable material characteristics.

Additionally, in some examples, the suture 110 (e.g., including the core region 112 and the cladding layer 114) may have a thickness suitable for suturing the biological tissue. Various thicknesses are possible and, in some examples, may be defined by the medical pharmacopeia. Example thicknesses may be as small as 0.01 mm or as large as 0.8 mm. However, other thicknesses for the suture 110 are possible that are less than 0.01 mm or greater than 0.8 mm in accordance with a type of the biological tissue being sutured. In an example scenario, the thickness may be associated with flexibility of the suture 110, and thus more flexible material characteristics (e.g., lower thickness) may facilitate forming a knot to tie the suture 110 after suturing the biological tissue.

Therefore, in some examples, the material characteristics of the suture 110 (e.g., the core region 112 and the cladding layer 114) may be selected based on a type of the biological tissue being sutured. For example, sutures for abdominal surgery may have different material characteristics than sutures for eye surgery. Accordingly, in some examples, the core region 112 and the cladding layer 114 may be configured to have the material characteristics (e.g., absorbability, thickness, flexibility, strength, elasticity, etc.) suitable for suturing one or more particular types of biological tissue. In some examples, the suture 110 may include other biological materials. For example, the core region 112 and/or the cladding layer 114 may include growth factors, drugs, etc. By way of example, where the suture 110 is an absorbable suture, such biological materials may be delivered to the biological tissue and/or other biological tissues gradually over time. Thus, for example, the suture 110 may be configured to allow controlled delivery of growth factors, drugs, etc., to facilitate healing of the biological tissue.

Additionally, in some examples, the material characteristics of the core region 112 and the cladding layer 114 may be selected such that the suture 110 may be configured as an optical fiber. Specifically, for example, the light source 104 may be optically coupled to the suture 110 to provide the light for propagation in the core region 112, and the material characteristics may cause the suture 110 to waveguide at least a portion of the received light inside the core region 112.

In an example embodiment, the core region 112 may include a first material of the suitable materials having a core index of refraction. Further, in the example embodiment, the cladding layer 114 may include a second material of the suitable materials having a cladding index of refraction. Additionally, for example, the first material and the second material may be configured to be at least partially transparent to one or more wavelengths of the light provided by the light source 104. In turn, for example, a difference between the core index of refraction and the cladding index of refraction may cause the at least portion of the light propagating in the core region 112 to reflect along an interface between the core region 112 and the cladding layer 114, thereby causing the at least portion of the light to be waveguided inside the core region 112. Additionally, for example, the core region 112 may have a core thickness and the cladding layer 114 may have a cladding layer thickness according to the suitable material characteristics. In particular, a sum of the core thickness and the cladding layer thickness may correspond to the thickness of the suture 110 suitable for the one or more particular types of biological tissue, for example. Moreover, in the example embodiment, the core thickness and the cladding layer thickness may also be selected to cause the at least portion of the light to be waveguided inside the core region 112.

Additionally, in some examples, the core region 112 and the cladding layer 114 may be configured to have the material characteristics (e.g., core thickness, cladding layer thickness, core index of refraction, cladding index of refraction, etc.) that also cause another portion of the light propagating in the core region 112 to propagate through the cladding layer 114 and out of the suture 110 to illuminate the suture 110. The portion propagating out of the suture 110 is illustrated in FIG. 1 as light 118. Accordingly, in some examples, the suture 110 may be configured as a "lossy" optical fiber (e.g., an optical fiber that leaks at least a threshold amount of light) based on the material characteristics of the core region 112 and the cladding layer 114.

Thus, in some examples, the suture 110 may have the material characteristics suitable for suturing the biological tissue, waveguiding light in the core region 112, and transmitting light out of the cladding layer 114. As an example of an absorbable suture 110, the core region 112 may include polyglycolic acid (e.g., core index of refraction ~1.45-151) and the cladding layer 114 may include polylactic acid (e.g., cladding index of refraction ~1.35-1.45). As an example of a non-absorbable suture 110, the core region 112 may include polyester (e.g., core index of refraction ~1.64-1.67) and the cladding layer 114 may include polypropylene (e.g., cladding index of refraction ~1.49). Other combinations of materials are possible.

Some embodiments of the present disclosure therefore provide sutures, such as the suture 110, that are illuminated by light (e.g., the light 118) that is propagating out of the sutures. In some examples, such mode of illumination may be advantageous. In a first example, modulation of the light 118 (e.g., color, intensity, etc.) may be adjusted (e.g., via the tuning device 106) to increase contrast between the suture 110 and the biological tissue being sutured. Additionally, in the first example, the modulation of the light 118 may correspond to a modulated light pattern to further enhance visibility (e.g., to allow dynamic tracing of the suture 110). In a second example, the suture 110 may be placed in a dark region, and the light 118 may improve the visibility of the dark region and the suture 110 (e.g., biological tissues around the suture 110 may also be more visible due to the light 118). Further, in the second example, the dark region may be included in a small space insufficient to receive an optic probe (e.g., external light source, camera, etc.), and thus the light 118 may enhance the visibility of the suture 118 in such small space. Other examples are possible.

To facilitate the propagation of the light 118 out of the suture 110, in some examples, the cladding layer 114 may optionally include a plurality of deformations 116. The deformations 116, for example, may increase the portion of the light propagating inside the core region 112 that propagates through the cladding layer 114 (e.g., the light 118) to illuminate the suture 110. Various implementations of the plurality of deformations 116 are possible. A non-exhaustive list of example implementations is presented below.

In one implementation, the plurality of deformations 116 may be formed during fabrication of the cladding layer 114. For example, the cladding layer thickness of the cladding layer 114 may be adjusted along various positions in the cladding layer 114 to form the plurality of deformations 116. Additionally or alternatively, for example, the cladding layer 114 may be configured to include a different material of the suitable suturing materials that has a different index of refraction than the cladding index of refraction of the cladding layer 114. For instance, the different material may be same as a material of the core 112, or may be another material that has a same or similar index of refraction. Thus, in this example, regions of the cladding layer 114 where the different material is included may correspond to the plurality of deformations 116.

In another implementation, the plurality of deformations 116 may be formed after the fabrication of the cladding layer 114. In a first example, mechanical friction (e.g., sandpaper, etc.) may be applied on the cladding layer 114 to form the deformations 116. In a second example, machining techniques (e.g., drilling, sawing, etc.) may be applied on the cladding layer 114 to form the deformations 116. In a third example, micro-fabrication techniques (e.g., laser etching, chemical etching, etc.) may be applied on the cladding layer 114 to form the plurality of deformations 116. Further, in the second and third examples, positions of the plurality of deformations 116 may be selected to enhance the visibility of the suture 110.

In some examples where the deformations 116 are not included in the cladding layer 114, a distribution of the light 118 propagating out of the suture 110 may not be uniform. For example, a larger amount of the light 118 may be propagating out of some regions of the suture 110 than an amount of the light 118 propagating out of other regions of the suture 110. Various reasons for such non-uniformity are possible. In one example, a modulation (e.g., wavelength, intensity, etc.) of the light provided by the light source 104 into the core region 112 may affect the amount of the light 118 propagating out of various regions of the suture 110. For example, a numerical aperture of the optical fiber (i.e., the suture 110) may cause particular wavelengths of the light 118 to propagate out of particular positions along a length of the suture 110. In another example, optical coupling of the light source 104 with the core region 112 may also affect the distribution of the light 118 (e.g., due to an acceptance angle of the optical fiber, a distance between the light source and a region of the suture 110, etc.). In yet another example, a shape of the suture 110 (e.g., due to flexibility) may also affect where the light 118 propagates out of the suture 110 (e.g., waveguided light inside the core region 112 may reach the cladding layer 114 at various angles, etc.).

Therefore, in some examples, the plurality of deformations 116 may be arranged in a given arrangement along a length of the cladding layer 114 to enhance the visibility of the suture 110. By way of example, the deformations 116 may be positioned in regions of the cladding layer 114 where a smaller amount of the light 118 may otherwise propagate out of the suture 110. Additionally or alternatively, for example, the plurality of deformations 116 may be variably spaced along the length of the cladding layer 114. For example, in regions of the cladding layer 114 where a large amount of the light 118 is expected to propagate out of the suture 110, a smaller number of the deformations 116 may be positioned to reduce the amount of the light 118 propagating out of such regions. Further, for example, in regions of the cladding layer 114 where a small amount of the light 118 is expected to propagate out of the suture 110, a larger number of the deformations 116 may be positioned to increase the amount of the light 118 propagating out of such regions.

Additionally or alternatively, in some examples, a distance between adjacent deformations of the plurality of deformations 116 may be based on a given distance from the adjacent deformations to a given end of the suture 110. For example, the light source 104 may be positioned proximal to the given end of the suture 110. In turn, for example, a larger amount of the light 118 may be expected to propagate out of regions of the suture 110 proximal to the given end. Thus, for example, spacing between adjacent deformations of the plurality of deformations 116 may be gradually decreased as the given distance from the adjacent formations to the given end increases to improve uniformity of the light 118.

However, in other examples, other schemes for spacing the plurality of deformations 116 are possible. For example, a relatively large amount of the light provided by the light source 104 may also propagate in regions proximal to an opposite end (e.g., opposite to the given end) of the suture 110. In particular, for example, some of the light from the light source 104 may exit from the core region 112 at the opposite end thereby illuminating the suture 110 at the opposite end. Thus, in these examples, adjacent deformations of the plurality of deformations 116 that are proximal to the opposite end may also be spaced accordingly to reduce the amount of the light 118 propagating out of such regions.

Although not illustrated in FIG. 1, in some examples, the suture 110 may also include a reflective device (e.g., mirror, slotted mirror, etc.) positioned at one or both ends of the suture 110. In turn, for example, the reflective device may cause at least a portion of the light propagating in the core region 112 towards the reflective device to reflect back into the core region 112, thereby increasing the amount of the light 118 propagating out of the cladding layer 114. Further, in some examples, the reflective device may be configured to selectively allow more light to enter into the core region 112 than light exiting the core region 112. For example, such selectivity may be achieved based on a modulation of the light (e.g., polarization, etc.).

Although not illustrated in FIG. 1, in some examples, the system 100 may include one or more additional illuminated sutures configured similarly to the suture 110 to further enhance visibility of the suture 110. For example, the one or more sutures may be configured as optical fibers that waveguide light having different modulation characteristics (e.g., colors, wavelengths, intensities, modulation patterns, etc.) to further enhance the visibility of the suture 110. The additional sutures, for example, may be coupled to the suture 110 (e.g., braiding, etc.).

The vision device 120 may be optionally included in the system 100 and configured to detect at least a portion of the light 118 propagating out of the suture 110. In some examples, the vision device 120 may include a body-mountable device such as goggles, eyeglasses, contact lens, etc., that include electronic components (e.g., sensor, etc.) configured to detect some or all of the light 118 and responsively provide or enhance visibility of the suture 110 (e.g., via a display included in the vision device 120, etc.) based on the detected portion of the light 118. In other examples, the vision device 120 may include an imaging system (e.g., computing device) that has a visual interface (e.g., display) for displaying the suture 110 and/or the biological tissue surrounding the suture 110 based on detection of the light 118. For example, the vision device 120 may be included in a robotic surgery system. Further, for example, the vision device 120 may be configured to detect the light 118 based on a modulation of the light 118 (e.g., frequency, pattern, etc.). In an example embodiment, the light 118 may include non-visible light (e.g., infrared, ultraviolet, etc.), and the vision device 120 may detect the non-visible light and render an image (or video) of the suture 110 and surrounding biological tissues to facilitate the suturing of the biological tissues. Further, for example, an output of the vision device 120 may be utilized to operate a robotic arm and/or components of the system 100 to perform the suturing and/or the surgery associated with the suturing.

Accordingly, in some examples, some or all of the components of the system 100 may be operated by a computing device to perform at least some of the functions described herein. For example, the computing device may be configured to execute program instructions stored in data storage of the computing device to cause the various components (e.g., suturing device 102, light source 104, tuning device 106, vision device 120, etc.) of the system 100 to perform the suturing of the biological tissue. Such computing device may be configured as a robotic surgery platform operated by a human operator (e.g., surgeon, nurse, technician, etc.) and/or a computer operator.

It is noted that the block diagram shown in FIG. 1 is described in connection with functional modules for convenience in description. For example, while the functional blocks in FIG. 1 shown as the suturing device 102 and the suture 110 may be implemented by separately packaged components coupled to one another, they do not necessarily need to be implemented as physically separated modules. Further, for example, the light source 104 may be a physically separate component or may be disposed in the suturing device 102 and/or the suture 110. Additionally, for example, the power supply 108 may be implemented as a separate physical component electrically or wirelessly coupled to the system 100.

Figure 2:
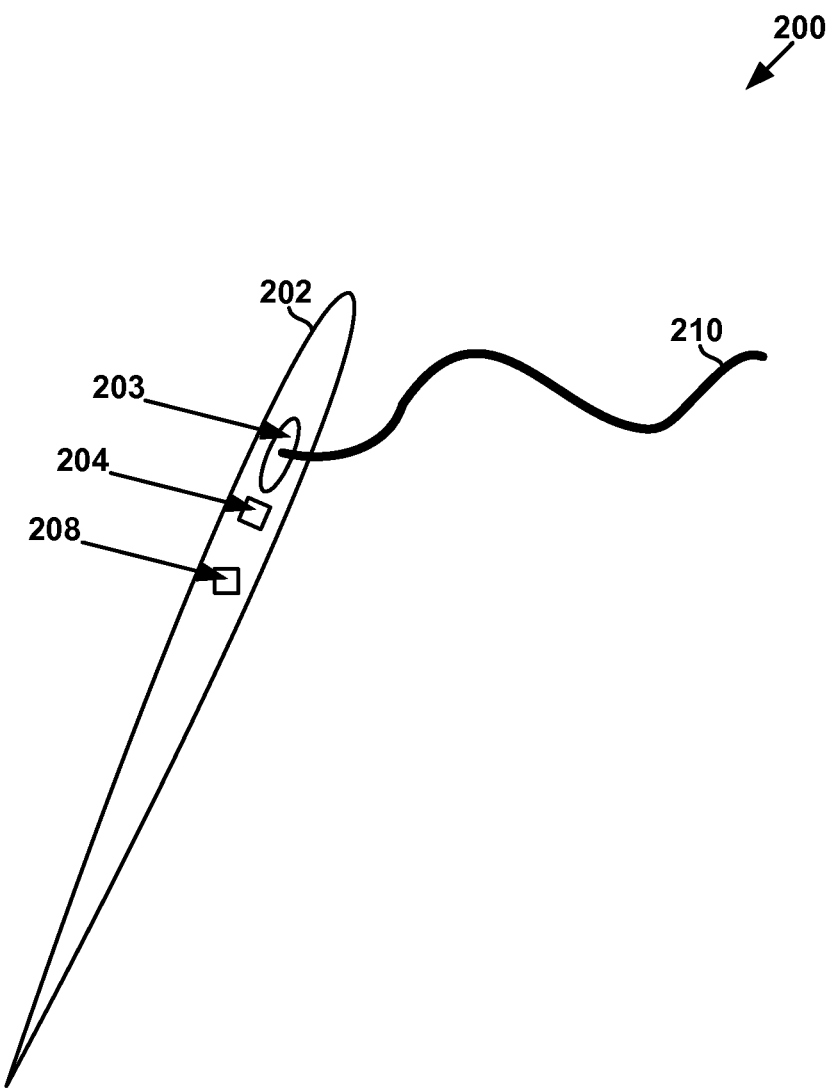
FIG. 2 illustrates a system that includes a surgical needle coupled to a suture, according to an example embodiment.

FIG. 2 illustrates a system 200 that includes a surgical needle 202 coupled to a suture 210, according to an example embodiment. It is noted that relative dimensions in the FIG. 2 are not necessarily to scale, but have been rendered for purposes of explanation only in describing the arrangement of the system 200. For example, a length of the suture 210 may be greater than length of the needle 202, etc. The function, structure, configuration, and arrangement of the system 200 may be similar to the system 100 of FIG. 1. For example, the surgical needle 202 may be configured similarly to the suturing device 102 to guide the suture 210 for suturing biological tissue. Further, for example, the suture 210 may be configured similarly to the suture 110 as an optical fiber having a core region and a cladding layer.

As illustrated in FIG. 2, the surgical needle 202 has a straight shape and a sharp edge for suturing the biological tissue. Alternatively, in some examples, the surgical needle 202 may have various shapes (e.g., ¼ circle, ⅜ circle, ½ circle, etc.) similarly to the suturing device 102 of the system 100. As illustrated in FIG. 2, the surgical needle 202 includes an indentation 203 for coupling the surgical needle 202 with the suture 210. In some examples, the indentation 203 may correspond to a hole drilled in the surgical 202 or a dent in the surgical needle 202. Further, in some examples, the indentation 203 may extend inside or along a surface of the surgical needle 202. For example, the suture 210 may be inserted into the indentation 203 such that the suture 210 may bend to a shape of the surgical needle 202. In this example, the surgical needle 202 may then be placed over damaged biological tissue and apply the suture 210 to the biological tissue for suturing. Other examples are possible. For example, although illustrated in FIG. 2 that an end of the suture 210 is coupled to the indentation 203 the suture 210 may be alternatively inserted through the indentation 203 and the surgical needle 202 may be crimped such that a middle portion of the suture 210 is coupled with the indentation 203.

Additionally, as illustrated in FIG. 2, the surgical needle 202 includes a light source 204 disposed on the surgical needle 202. The light source 204 may be similar to the light source 104 (e.g., LED, LCD, etc.) and may be configured to provide light that propagates inside the suture 210. Additionally, in some examples, a portion of the light provided by the light source 204 may propagate out of an outer surface of the suture 210 similarly to the light 118 of the system 100. Although FIG. 2 shows the light source 204 disposed adjacent to the indentation 203, in some examples, the light source 204 may be disposed in other positions. In one example, the light source 204 may be disposed in the indentation 203. In another example, the light source 204 may be disposed in the suture 210. For example, the light source 204 may be optically coupled to one or both ends of the suture 210 to provide light that propagates inside the suture 210. Other positions for optically coupling the light source 204 to the suture 210 are possible as well.

In some examples, the suture 210 may include a plurality of deformations similarly to the deformations 116 of the suture 110. In such examples, the light source 204 may be arranged to provide the light through one or more of the plurality of deformations. Further, the suture 210 may include a reflective device (e.g., mirror) positioned at one or both ends of the suture 210 to reflect part of the light directed towards the one or both ends back into the suture 210. In this way, an amount of light propagating out of other parts of the suture 210 (e.g., middle portion etc.) may be increased.

The surgical needle 202 also includes a power supply 208 electrically coupled to the light source 204 and configured to power the light source 204. For example, the power supply 208 may include one or more electrochemical cells coupled to the light source 204 (e.g., via interconnects, etc.) in the surgical needle 202. In some examples, the assembly illustrated in the system 200 may be sterilized and stored in a vacuum-sealed container. In these examples, the power supply 208 may include a sensor for detection of oxygen to responsively activate the light source 204 when the container is opened.

The suture 210 may have material characteristics suitable for suturing biological tissue similarly to the suture 110 of the system 100. For example, the suture 210 may have thickness, flexibility, strength, absorbability, etc., suitable for suturing one or more particular biological tissues. Further, in some examples, the suture 210 may receive the light from the light source 204, waveguide a portion of the light along a length of the suture 210, and allow another portion of the light to propagate out of an outer surface of the suture 210 to illuminate the suture 210.

Figure 3A:
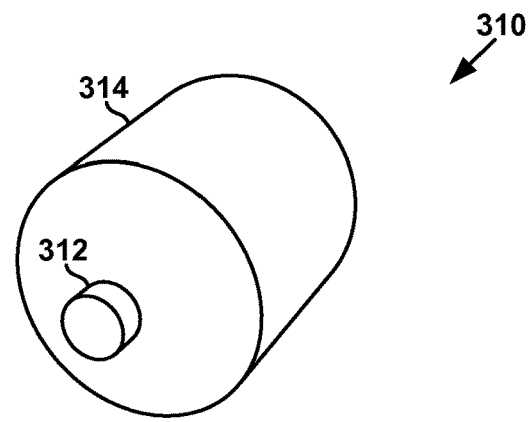
FIG. 3A illustrates a suture, according to an example embodiment.
Figure 3B:
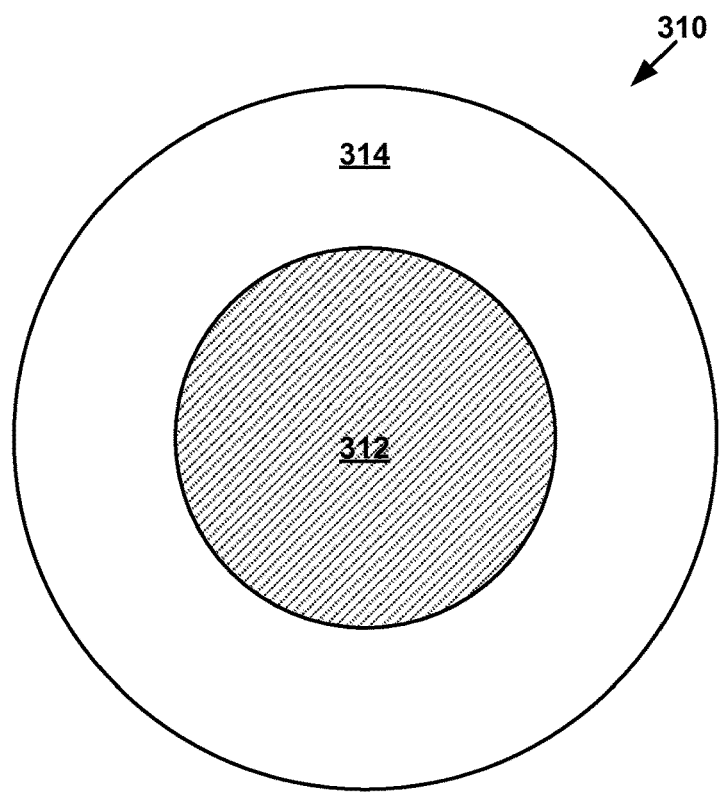
FIG. 3B illustrates a cross-section view of the suture in FIG. 3A.

FIG. 3A illustrates a suture 310, according to an example embodiment. FIG. 3B illustrates a cross-section view of the suture 310 in FIG. 3A. The suture 310 may be configured similarly to the sutures 110 and 210 of the systems 100 and 200. Thus, the suture 310 illustrated in FIG. 3A may correspond to an example embodiment of the suture 110 described in the system 100. For example, the suture 310 includes a core region 312 and a cladding layer 314 that may correspond, respectively, to the core region 112 and the cladding layer 114 of the system 100. It is noted that relative dimensions in the FIGS. 3A and 3B are not necessarily to scale, but have been rendered for purposes of explanation only in describing the arrangement of the system 300. For example, a core thickness of the core region 312 relative to a cladding layer thickness of the cladding layer 314 may be different than the illustrations of FIGS. 3A and 3B.

Additionally, the core region 312 and the cladding layer 314 may have material characteristics suitable for suturing one or more particular biological tissues, similarly to the material characteristics of the core region 112 and the cladding layer 114. In one example, the core region 312 and the cladding layer 314 may include absorbable materials that are configured to degrade gradually as the biological tissue heals. For example, the absorbable materials may include polymers such as polyglycolic acid, polylactic acid, polydioxanone, etc. In another example, the core region 312 and the cladding layer 314 may include non-absorbable materials that are suitable for suturing the biological tissue. For example, the non-absorbable materials may include synthetic polymers such as polypropylene, polyester, nylon, etc.

Further, in some examples, the core thickness of the core region 312 and the cladding layer thickness of the cladding layer 314 may also be configured in accordance with the material characteristics suitable for suturing the one or more particular biological tissues (e.g., diameter, flexibility, strength, etc.). For example, the suture 310 may have a diameter of 0.5 mm based on the core thickness being 0.3 mm and the cladding layer thickness being 0.2 mm. Other dimensions are possible similarly to the suture 110 of the system 100.

Additionally, the core region 312 and the cladding layer 314 may be configured such that the suture 310 corresponds to an optical fiber. For example, the core region 312 may be formed from a first polymer having a core index of refraction, and the cladding layer 314 may be formed from a second polymer having a cladding index of refraction. In turn, for example, a portion of light propagating in the core region 312 may be waveguided inside the core region 312 due to a difference between the core index of refraction and the cladding index of refraction. Moreover, for example, another portion of the light may propagate out of the cladding layer 314 to illuminate the suture 310 similarly to the light 118 of the system 100.

Therefore, in accordance with the present disclosure, the suture 310 may provide both functionalities of an illuminated optical fiber and a surgical suture having the material characteristics suitable for suturing biological tissue, for example.

Figure 4:
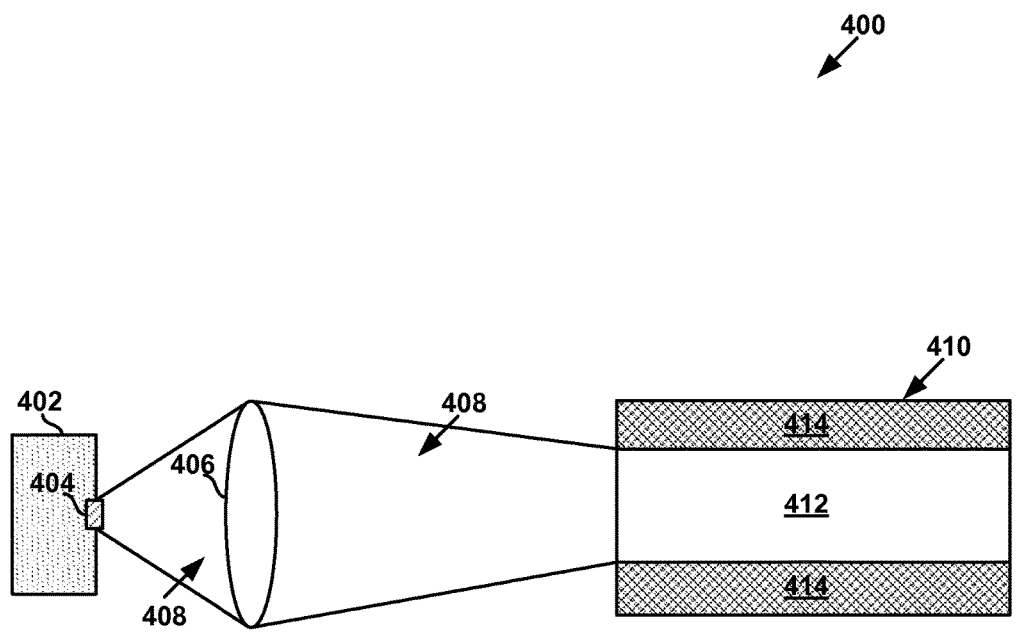
FIG. 4 illustrates a system for illuminating a suture, according to an example embodiment.

FIG. 4 illustrates a system 400 for illuminating a suture 410, according to an example embodiment. The system 400 includes a support structure 402, a light source 404, an optical element 406, and the suture 410. The functions of at least some components of the system 400 may be similar to components in the system 100. For example, the light source 404 and the suture 410 may be similar, respectively, to the light source 104 and the suture 110 of the system 100.

The support structure 402 may include any structure configured to support the light source 404. For example, the support structure 402 may include a substrate comprising solid materials (e.g., copper, plastic, metal, etc.) that has mechanical properties sufficient to support the light source 404. Further, in some examples, the support structure 402 may include one or more interconnects for providing power to the light source 404 from a power supply (not illustrated in FIG. 4).

The light source 404 may include various types of light sources (e.g., LED, OLED, LCD, etc.) similarly to the light source 104 of the system 100. Further, as illustrated in FIG. 4, the light source 404 may be configured to provide light 408 that is coupled into and propagates through the suture 410. For example, the light source 404 may receive a modulated power input, and may responsively emit the light 408 directed towards the suture 410.

The optical element 406 may include one or more optical elements such as lens, prisms, filters, a combination of these, etc., configured to direct, focus, and/or adjust modulation of the light 408 into the suture 410. Thus, in some examples, the optical element 406 may be configured to facilitate optical coupling of the light source 404 into the suture 410. In some examples, the optical element 406 may be implemented as a same physical component with the light source 404 and/or the suture 410. In other examples, the optical element 406 may be implemented as a separate component mechanically and optically coupled between the light source 404 and the suture 410.

The function and structure of the suture 410 may be similar to the sutures 110, 210, and 310 that are illustrated, respectively, in FIGS. 1, 2, and 3A/3B. For example, the suture 410 includes a core region 412 and a cladding layer 414 that have material characteristics suitable for suturing biological tissue. Additionally, for example, the material characteristics of the core region 412 and the cladding layer 414 may be configured to also cause the suture 410 to operate as an optical fiber. For example, as illustrated in FIG. 4, the optical element 406 may direct the light 408 provided by the light source 404 into the core region 412. In turn, for example, a portion of the light 408 may propagate inside the core region 412 and another portion of the light 408 may propagate out of the cladding layer 414 due to the material characteristics (e.g., index of refraction, thickness, etc.) of the core region 412 and the cladding layer 414.

Other arrangements of the light source 404 and/or the optical element 406 are possible. Although illustrated in FIG. 4 that the light 408 enters the core region 412 at an end of the suture 410, in some examples, the light source 404 and/or the optical element 406 may be arranged differently such that the light 408 enters the suture 410 at a different position. For example, the cladding layer 414 may include one or more deformations similarly to the deformations 116 of the system 100. In turn, for example, the light 408 may be directed by the optical element 406 into one or more of the deformations towards the core region 412. Thus, in some examples, the system 400 may be configured to direct the light 408 into the core region 412 in various positions along a length of the suture 410.

Figure 5:
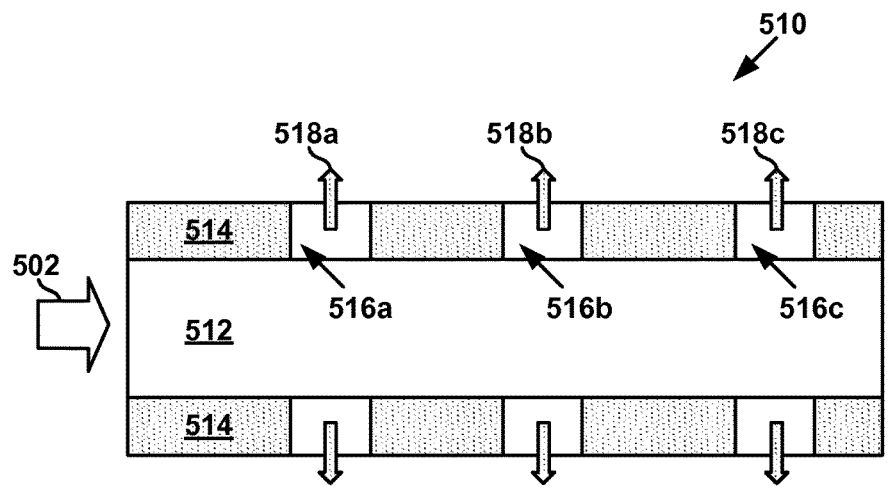
FIG. 5 illustrates a suture that includes a cladding layer having a plurality of deformations, according to an example embodiment.

FIG. 5 illustrates a suture 510 that includes a cladding layer 514 having a plurality of deformations 516a-c, according to an example embodiment. The suture 510 includes a core region 512, the cladding layer 514, and the plurality of deformations 516a-c.

The function and structure of the suture 510 may be similar to the sutures 110, 210, 310, and 410 that are illustrated, respectively, in FIGS. 1, 2, 3A/3B, and 4. For example, the core region 512 and the cladding layer 514 may have material characteristics suitable for suturing biological tissue similarly to the core region 112 and the cladding layer 114 of the system 100. Additionally, for example, the material characteristics of the core region 512 and the cladding layer 514 may be configured to also cause the suture 510 to operate as an optical fiber. For example, as illustrated in FIG. 5, light 502 may be provided by a light source similar to the light source 104 of the system 100 into the core region 512. In turn, for example, a portion of the light 502 may be waveguided inside the core region 512 and another portion of the light 502, illustrated in FIG. 5 as light 518a-c, may propagate out of the cladding layer 514 due to the material characteristics (e.g., index of refraction, thickness, etc.) of the core region 512 and the cladding layer 514.

Additionally, as illustrated in FIG. 5, the suture 510 includes the plurality of deformations 516a-c to facilitate propagation of the light 518a-c through the cladding layer 514 and out of the suture 510. In turn, for example, the light 518a-c may illuminate the suture 510 to enhance visibility of the suture 510. Various configurations are possible for the deformations 516a-c similarly to the deformations 116 of the system 100. In one example, the deformations 516a-c may correspond to removed and/or distorted portions of the cladding layer 514. In this example, the deformations 516a-c may be formed using various techniques such as mechanical friction (e.g., sandpaper, etc.), machining, etching, etc. In another example, the deformations 516a-c may correspond to materials having a same or similar index of refraction as the core region 512. For example, the deformations 516a-c may include a same polymer as the core region 512 or another polymer having a similar (or same) index of refraction. In yet another example, the deformations 516a-c may correspond to areas of the cladding layer 514 having a smaller thickness than other areas of the cladding layer 514.

Figure 6:
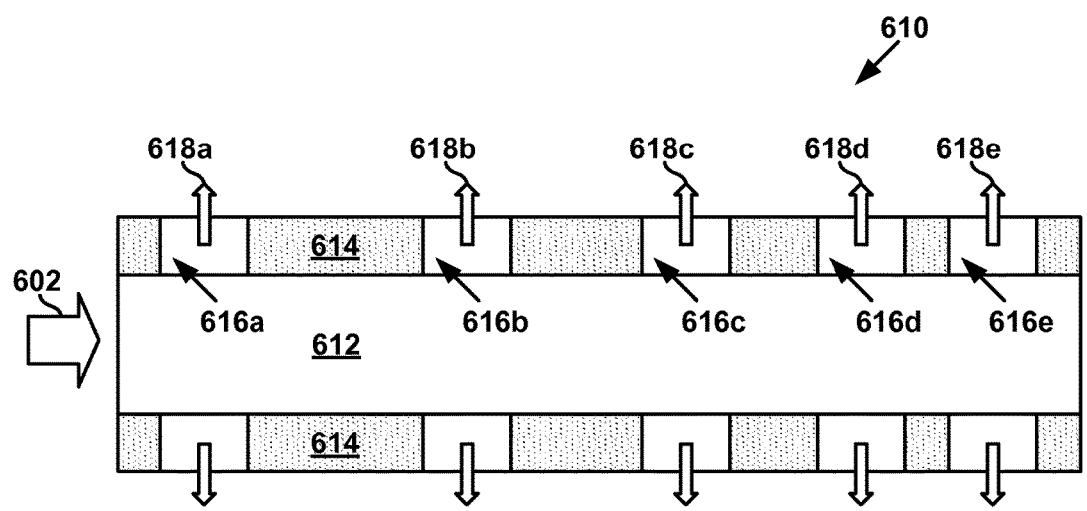
FIG. 6 illustrates a suture that includes a cladding layer having a plurality of variably spaced deformations, according to an example embodiment.

FIG. 6 illustrates a suture 610 that includes a cladding layer 614 having a plurality of variably spaced deformations 616a-e, according to an example embodiment. The suture 610 includes a core region 612, the cladding layer 614, and the plurality of deformations 616a-e.

The function and structure of the suture 610 may be similar to the sutures 110, 210, 310, 410, and 510 that are illustrated, respectively, in FIGS. 1, 2, 3A/3B, 4, and 5. For example, the core region 612 and the cladding layer 614 may have material characteristics suitable for suturing biological tissue similarly to the core region 112 and the cladding layer 114 of the system 100. Additionally, the material characteristics of the core region 612 and the cladding layer 614 may be configured to also cause the suture 610 to operate as an optical fiber similarly to the suture 510, for example.

Additionally, as illustrated in FIG. 6, the suture 610 includes the plurality of deformations 616a-e to facilitate propagation of the light 618a-e through the cladding layer 614 and out of the suture 610. In turn, for example, the light 618a-e may illuminate the suture 610 to enhance visibility of the suture 610, similarly to the light 518a-c of the suture 510. Various configurations are possible for the deformations 616a-e similarly to the deformations 516a-c of the suture 510.

Additionally, as illustrated in FIG. 6, the deformations 616a-e may be variably spaced along the cladding layer 614 to enhance uniformity of the light 618a-e propagating out of the suture 610. In an example scenario, the light 618e propagating out of the deformation 616e may have a lower amount, intensity, brightness, etc., than the 618a propagating out of the deformation 616a. In the example scenario, such discrepancy may be caused by various factors as discussed in the description of the plurality of deformations 116 of the system 100. For example, an amount of the light 618a propagating out of the deformation 616a may be greater due to the deformation 616a being closer to a source of the light 602 than the deformation 616e. Accordingly, in some examples, the deformations 616a-e may be variably spaced to enhance the uniformity of the light 618a-e. As illustrated in FIG. 6, in the example scenario, a distance between adjacent deformations 618d and 618e may be configured to be smaller than a distance between adjacent deformations 618a and 618b.

Additionally or alternatively, in some examples, a distance between adjacent deformations may be based on a given distance from the adjacent deformations to a given end of the suture 610. For example, the distance between adjacent deformations may be reduced gradually as the given distance increases. As illustrated in FIG. 6, for example, the distance between the deformations 618a and 618b is greater than the distance between the deformations 618b and 618c that is also, in turn, greater than the distance between the deformations 618c and 618d, etc. Therefore, for example, where the given end is proximal to the source of the light 602, the spacing between adjacent deformations of the deformations 618a-e may be gradually reduced based on the given distance between the adjacent deformations and the given end, as illustrated in FIG. 6.

Figure 7:
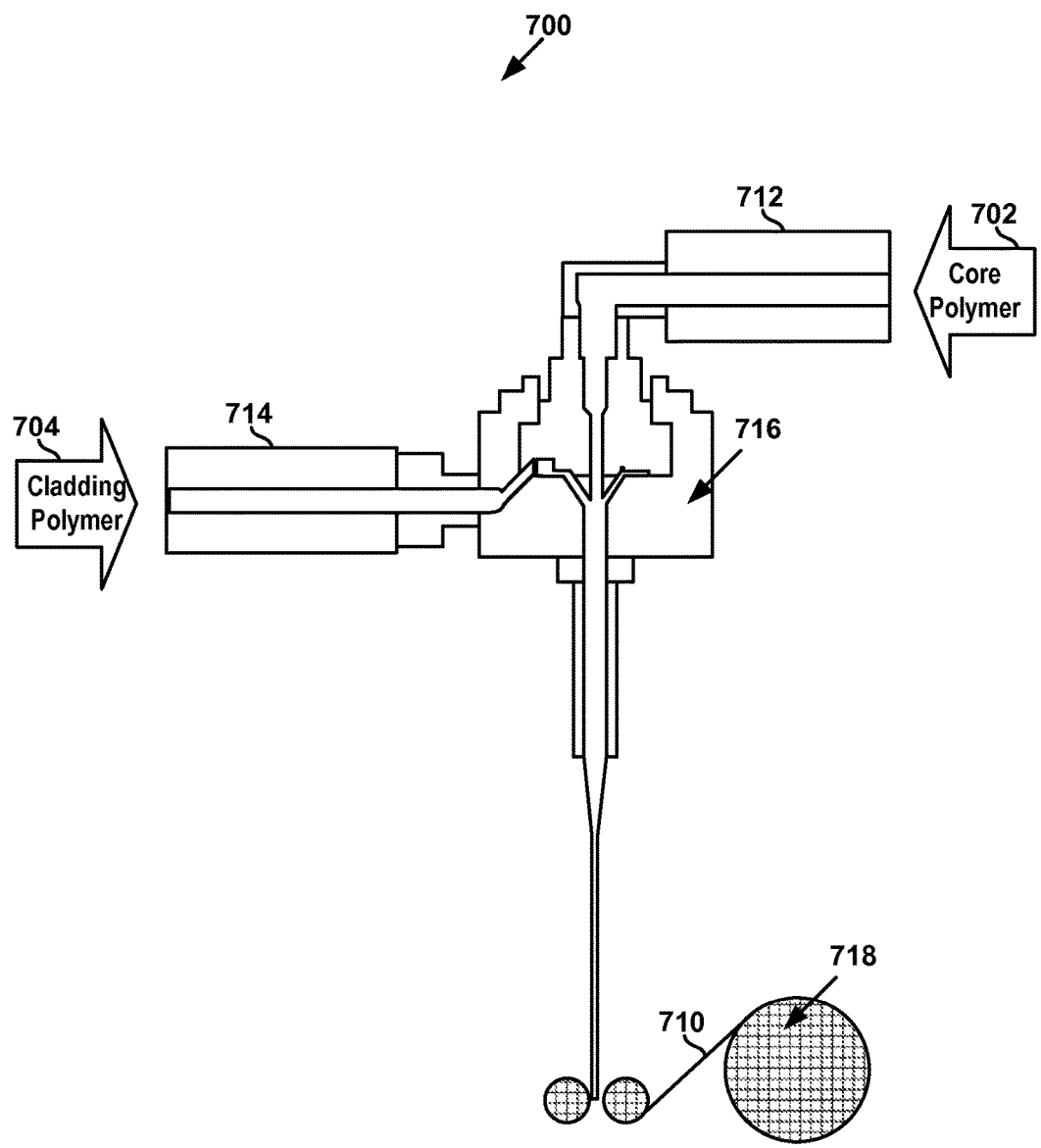
FIG. 7 illustrates an apparatus for forming a suture, according to an example embodiment.

FIG. 7 illustrates an apparatus 700 for forming a suture 710, according to an example embodiment. The apparatus 700 includes a core extrusion section 712, a cladding extrusion section 714, a diffusion section 716, and a reel 718.

The core extrusion section may be configured to receive a core polymer 702 and to heat the core polymer 702 to a liquid state (e.g., melt). Similarly, the cladding extrusion section may be configured to receive a cladding polymer 704 and to heat the cladding polymer 704 to a liquid state. The liquid core polymer 702 and the liquid cladding polymer 704 may then be combined in the diffusion section 716 to form the suture 710. The reel 718 may be configured to rotate at a given speed to adjust a thickness of the suture 710. In turn, the suture 710 may have material characteristics suitable for suturing biological tissue and also suitable for the suture 710 to operate as an optical fiber, similarly to the sutures 110, 210, 310, 410, 510, and 610. For example, the core polymer 702 and the cladding polymer 704 may have the material characteristics (e.g., strength, absorbability, etc.) suitable for the suturing and the material characteristics suitable for waveguiding light (e.g., index of refraction, core thickness, cladding layer thickness, deformations, etc.).

Additionally, in some examples, the core extrusion section 712 and/or the cladding extrusion section 714 may be configured to provide, respectively, the core polymer 702 and the cladding polymer 704 to the diffusion section 716 at a rate that causes the suture 710 to have a core region and a cladding layer having an appropriate thickness. Further, in some examples, the diffusion section 716 may adjust a temperature of the combination of the core polymer 702 and the cladding polymer 704 to modify mechanical and/or optical properties of the suture 710 (e.g., including properties of the core region and the cladding layer).

In some examples, a plurality of deformations in the cladding layer of the suture 710 may be formed by the apparatus 700. In one example, the cladding extrusion section 714 may be configured to intermittently adjust a rate of provision of the cladding polymer 704 to the diffusion section 716. In turn, for example, the suture 710 may have little or no cladding polymer 704 in various positions along the suture 710 that correspond to the plurality of deformations. Further, for example, a thickness of the cladding layer of the suture 710 may be intermittently varied, similarly, to form the plurality of deformations. In another example, the cladding extrusion section 714 may be configured to intermittently provide a given polymer other than the cladding polymer 704 to the diffusion section 716. For example, the given polymer may correspond to the core polymer 702 or may be another polymer having a same or similar index of refraction as the core polymer 702. Thus, in this example, the suture 710 may also be formed to have regions of the cladding layer that correspond to the plurality of deformations. In yet another example, the diffusion section 716 may intermittently adjust the temperature of the cladding polymer 704 to modify the refractive index of the cladding polymer 704 at various locations in the cladding layer of the suture 710. In this example, such locations may correspond to the plurality of deformations.

Figure 8:
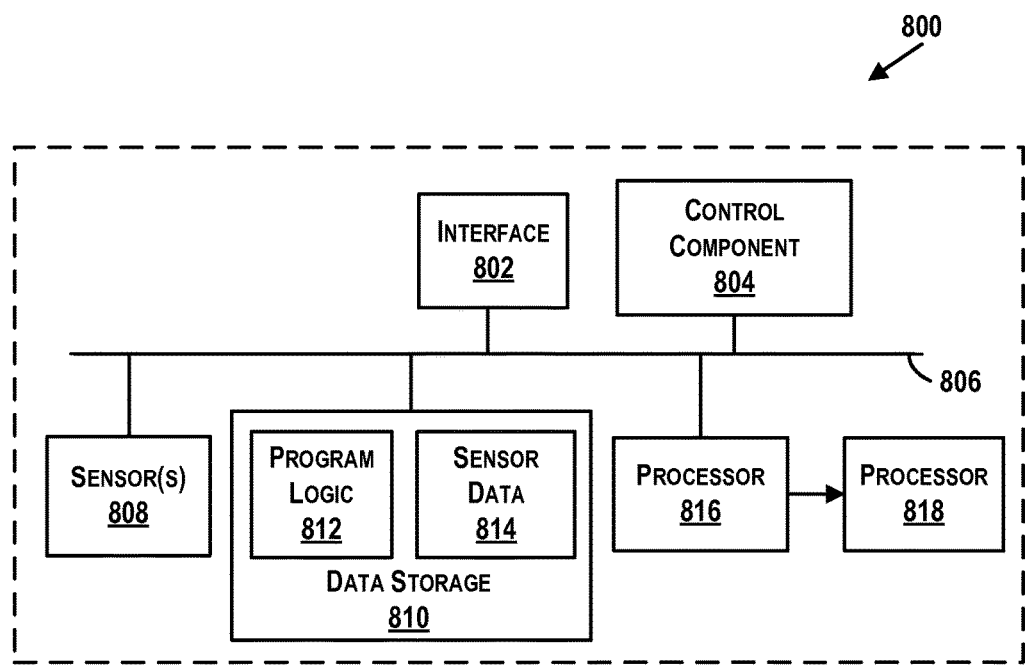
FIG. 8 is a block diagram of a computing device, according to an example embodiment.

FIG. 8 is a block diagram of a computing device 800, according to an example embodiment. The computing device 800 may be configured to operate at least some components of the systems, devices, and/or apparatuses illustrated in FIGS. 1-7. In one example, the computing device 800 may correspond to a robotic surgery platform to operate components such as the suturing device 102, the light source 104, the tuning device 106, the vision device 108, etc. In another example, the computing device 800 may be configured to assist operation of one or more components such as the tuning device 106 (e.g., for modulation of light from light source 104, etc.)), the vision device 120 (e.g., for processing non-visible light, etc.), or any other component. In yet another example, the computing device 800 may be configured to operate the apparatus 700 to form the suture 710 (e.g., for intermittently adjusting output of the cladding extrusion section, etc.). Other examples are possible.

In some examples, some components illustrated in FIG. 8 may be distributed across multiple computing devices (e.g., desktop computers, servers, hand-held devices, etc.). However, for the sake of example, the components are shown and described as part of one example device 800.

The device 800 may include an interface 802, a control component 804, sensor(s) 808, data storage 810, and a processor 816. Components illustrated in FIG. 8 may be linked together by a communication link 806. In some examples, the device 800 may include hardware to enable communication within the device 800 and between the device 800 and another computing device (not shown), such as a device included in a suturing system (e.g., system 100, etc.) or an apparatus for forming a suture (e.g., apparatus 700, etc.). The hardware may include transmitters, receivers, and antennas, for example.

The interface 802 may be configured to allow the device 800 to communicate with another computing device (not shown), such as a suturing device, tuning device, etc. Thus, the interface 802 may be configured to receive input data from one or more devices, and may also be configured to send output data to the one or more devices. In some examples, the interface 802 may also maintain and manage records of data received and sent by the device 800. In other examples, records of data may be maintained and managed by other components of the device 800. The interface 802 may also include a receiver and transmitter to receive and send data. In some examples, the interface 802 may also include a user-interface, such as a keyboard, microphone, touch screen, etc., to receive inputs as well. Further, in some examples, the interface 802 may also include interface with output devices such as a display, speaker, etc.

The control component 804 may be a hardware interface that is configured to facilitate output of control signals for various devices and apparatuses of the present disclosure. For example, the control component 804 may include circuitry that operates the suturing device 102 of the system 100, or a communication interface (e.g., USB, HDMI, etc.) to couple the vision device 120 with the device 800. Other examples are also possible such as wireless communication interfaces (e.g., Wi-Fi, Bluetooth, etc.).

The sensor 808 may include one or more sensors, or may represent one or more sensors included in the device 800. Example sensors include photodetectors, light sensors, microphones, cameras, pressure sensors, and/or other sensors. Referring back to FIG. 1, for example, the sensors 808 may include sensors of the vision system 120 that detect light 118. Additionally, the sensor 808 may include sensors for measuring distance such as a camera, motion detector, infrared range sensor, radar, lidar, or other distance measuring sensor. Such sensors of the sensor 808 may facilitate operating a robotic arm, for example, to operate a suturing device (e.g., the suturing device 102).

The processor 816 may be configured to operate the device 800. For example, the processor 816 may be configured to cause the device 800 to provide instructions to the control component 804 to operate a suturing system. Further, the processor 816 may also be configured to operate other components of the device 800 such as input/output components or communication components. The device 800 is illustrated to include an additional processor 818. The processor 818 may be configured to control some of the aspects described for the processor 816. For example, the processor 816 may be a controller that operates the control component 804, and the processor 818 may be configured to control other aspects such as the sensors 808. Some embodiments may include only one processor (e.g., processor 816) or may include additional processors configured to control various aspects of the device 800.

The data storage 810 may store program logic 812 that can be accessed and executed by the processor 816 and/or the processor 818. For example, the program logic 812 may include instructions for any of the functions described herein for the system 100 or any component thereof, such as suturing device 102, the tuning device 106, and/or the vision system 120. Additionally or alternatively, for example the program logic 812 may include any of the functions described herein for the apparatus 700. The data storage 810 may also store collected sensor data 814 that may include data collected by any of the sensors 808. For example, the sensor data 814 may indicate detected light propagating out of a suture (e.g., light 118 in FIG. 1), and the computing device 800 may process the sensor data to render an image of the suture and surrounding biological tissues.

The communication link 806 is illustrated as a wired connection; however, wireless connections may also be used. For example, the communication link 806 may be a wired serial bus such as a universal serial bus or a parallel bus, or a wireless connection using, e.g., short-range wireless radio technology, communication protocols described in IEEE 802.11 (including any IEEE 802.11 revisions), or cellular wireless technology, among other possibilities.

Figure 9:
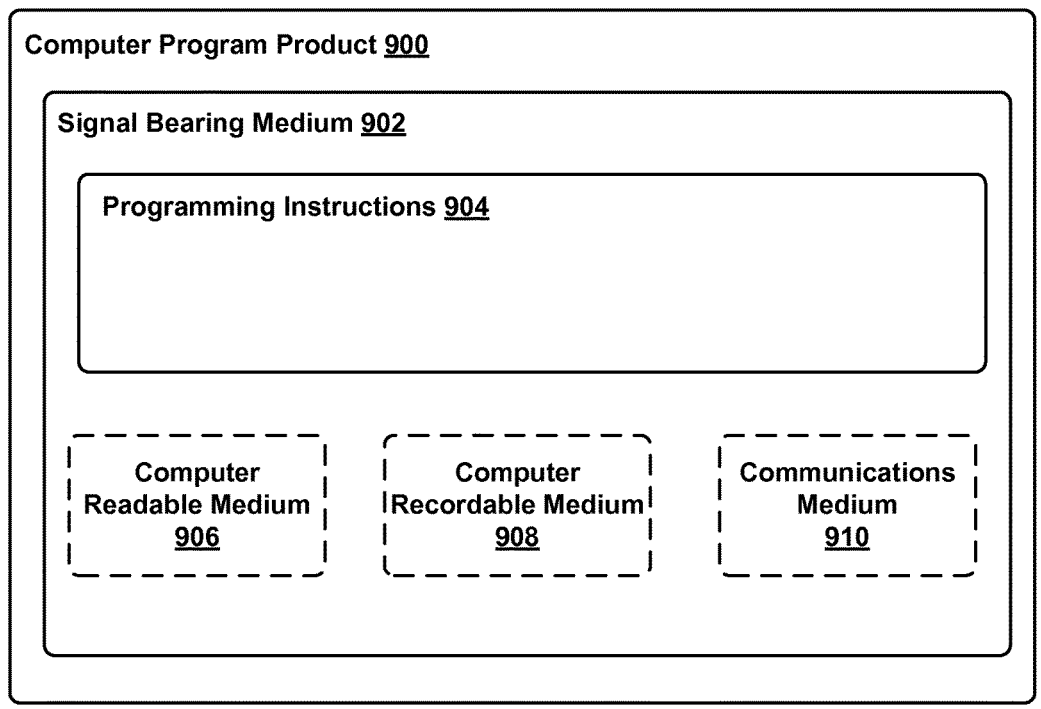
FIG. 9 depicts an example computer readable medium configured according to an example embodiment.

FIG. 9 depicts an example computer readable medium configured according to an example embodiment. In example embodiments, an example system may include one or more processors, one or more forms of memory, one or more input devices/interfaces, one or more output devices/interfaces, and machine readable instructions that when executed by the one or more processors cause the system to carry out the various functions tasks, capabilities, etc., described above.

As noted above, in some embodiments, the disclosed techniques (e.g., functions of the system 100, apparatus 700, etc.) may be implemented by computer program instructions encoded on a computer readable storage media in a machine-readable format, or on other media or articles of manufacture (e.g., program logic 810 of the device 800). FIG. 9 is a schematic illustrating a conceptual partial view of an example computer program product that includes a computer program for executing a computer process on a computing device, arranged according to at least some embodiments disclosed herein.

In one embodiment, the example computer program product 900 is provided using a signal bearing medium 902. The signal bearing medium 902 may include one or more programming instructions 904 that, when executed by one or more processors may provide functionality or portions of the functionality described above with respect to FIGS. 1-8. In some examples, the signal bearing medium 902 may be a computer-readable medium 906, such as, but not limited to, a hard disk drive, a Compact Disc (CD), a Digital Video Disk (DVD), a digital tape, memory, etc. In some implementations, the signal bearing medium 902 may be a computer recordable medium 908, such as, but not limited to, memory, read/write (R/W) CDs, R/W DVDs, etc. In some implementations, the signal bearing medium 902 may be a communication medium 910 (e.g., a fiber optic cable, a waveguide, a wired communications link, etc.). Thus, for example, the signal bearing medium 902 may be conveyed by a wireless form of the communications medium 910.

The one or more programming instructions 904 may be, for example, computer executable and/or logic implemented instructions. In some examples, a computing device may be configured to provide various operations, functions, or actions in response to the programming instructions 904 conveyed to the computing device by one or more of the computer readable medium 906, the computer recordable medium 908, and/or the communications medium 910.

The computer readable medium 906 may also be distributed among multiple data storage elements, which could be remotely located from each other. The computing device that executes some or all of the stored instructions could be an external computer, or a mobile computing platform, such as a smartphone, tablet device, personal computer, wearable device, etc. Alternatively, the computing device that executes some or all of the stored instructions could be remotely located computer system, such as a server.

It should be understood that arrangements described herein are for purposes of example only. As such, those skilled in the art will appreciate that other arrangements and other elements (e.g. machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location, or other structural elements described as independent structures may be combined.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims, along with the full scope of equivalents to which such claims are entitled. It is also to be understood that the terminology used herein is for the purpose of describing particular embodiments only, and is not intended to be limiting.

What is claimed is:

1. An apparatus comprising:
    an optical fiber having material characteristics suitable for suturing biological tissue,
    wherein the optical fiber comprises a core region having a core thickness and a core index of refraction that allows light to propagate in the core region,
    wherein the optical fiber comprises a cladding layer having a cladding layer thickness and at least a portion of the cladding layer having a cladding index of refraction different than the core index of refraction such that the optical fiber guides propagation of the light inside the core region,
    wherein the optical fiber transmits, based on at least the core thickness and the cladding layer thickness, at least a first portion of the light propagating in the core region out of the optical fiber through the cladding layer to illuminate the optical fiber and the biological tissue,
    wherein the optical fiber comprises a plurality of deformations in the cladding layer, the plurality of deformations corresponding to portions of the cladding layer that comprise a same index of refraction as the core index of refraction, and
    wherein a second portion of the light propagates out of the cladding layer through the plurality of deformations;
    a light source optically coupled to the optical fiber to provide the light for propagation in the core region of the optical fiber,
    wherein the plurality of deformations are arranged such that a distance between adjacent deformations is based on a given distance from the adjacent deformations to the light source; and
    a suturing device coupled to the optical fiber to guide the optical fiber for suturing the biological tissue.

2. The apparatus of claim 1, wherein the plurality of deformations corresponds to removed portions of the cladding layer.

3. The apparatus of claim 1, further comprising:
    a tuning device coupled to the light source to adjust one or more of a wavelength or intensity of the light provided by the light source.

4. The apparatus of claim 3, wherein the tuning device modulates the light provided by the light source to correspond to a given modulated light pattern.

5. The apparatus of claim 1, further comprising:
    at least one other optical fiber coupled to the optical fiber,
    wherein modulated light from at least one other light source propagates out of a given cladding layer of the at least one other optical fiber, and
    wherein the modulated light has a wavelength other than a corresponding wavelength of the light from the light source.

6. The apparatus of claim 1, wherein the suturing device comprises a surgical needle, wherein the light source is disposed on the surgical needle.

7. The apparatus of claim 1, wherein the light source is disposed in the optical fiber.

8. The apparatus of claim 1, further comprising:
    a vision device that detects the at least first portion of the light propagating out of the optical fiber.

9. The apparatus of claim 1, further comprising:
    a sensor for detecting oxygen; and
    a power supply that powers the light source responsive to the sensor detecting oxygen.

10. The apparatus of claim 1, wherein the core region and the cladding layer comprise absorbable materials.

11. The apparatus of claim 1, wherein the core region and the cladding layer comprise non-absorbable materials.

12. A suture comprising:
    a core polymer having a core thickness, wherein the core polymer has a core index of refraction to allow light to propagate in the core polymer;
    a cladding polymer having a cladding thickness,
    wherein the cladding polymer is coupled to an outer surface of the core polymer,
    wherein at least a portion of the cladding polymer has a cladding index of refraction different than the core index of refraction such that a first portion of the light propagating in the core polymer is guided inside the core polymer,
    wherein the core polymer and the cladding polymer have material characteristics suitable for suturing biological tissue, and
    wherein the suture transmits, based on at least the core thickness and the cladding thickness, a second portion of the light propagating in the core polymer through the cladding polymer and out of the suture to illuminate the suture and the biological tissue; and
    a plurality of deformations in the cladding polymer corresponding to portions of the cladding layer that comprise a same index of refraction as the core index of refraction, wherein the second portion of the light propagates out of the cladding polymer through the plurality of deformations, wherein the plurality of deformations are variably spaced along the cladding polymer to enhance uniformity of light propagating out of the suture by gradually reducing a distance between adjacent deformations as a given distance increases from a given end of the suture.

13. The suture of claim 12, wherein the plurality of deformations corresponds to removed portions of the cladding polymer.

14. The suture of claim 12, further comprising:
a light source disposed in the suture to provide the light for propagation in the core polymer.

15. The suture of claim 14, further comprising:
a sensor for detecting oxygen; and
a power supply that powers the light source responsive to the sensor detecting oxygen.

16. A suturing device comprising:
a surgical needle having an indentation to couple an optical fiber that has material characteristics suitable for suturing biological tissue,
wherein the optical fiber comprises a core region having a core thickness and a core index of refraction that allows light to propagate in the core region,
wherein the optical fiber comprises a cladding layer having a cladding layer thickness and at least a portion of the cladding layer having a cladding index of refraction different than the core index of refraction such that the optical fiber guides the light propagating inside the core region,
wherein the optical fiber transmits, based on at least the core thickness and the cladding layer thickness, at least a first portion of light propagating in the core region to propagate out of the optical fiber through the cladding layer to illuminate the suture and the biological tissue,
wherein the optical fiber comprises a plurality of deformations in the cladding layer, the plurality of deformations corresponding to portions of the cladding layer that comprise a same index of refraction as the core index of refraction, and
wherein a second portion of the light propagates out of the cladding layer through the plurality of deformations; and
a light source disposed on the surgical needle, wherein the light source is optically coupled to the optical fiber and provides the light for propagation in the core region of the optical fiber,
wherein the plurality of deformations are arranged such that a distance between adjacent deformations is based on a given distance from the adjacent deformations to the light source.

17. The suturing device of claim 16, wherein the light source is disposed in the indentation.

18. The suturing device of claim 16, wherein the light source is disposed adjacent to the indentation.

* * * * *